United States Patent
Mitts et al.

(10) Patent No.: US 6,777,389 B1
(45) Date of Patent: Aug. 17, 2004

(54) COSMETIC OR DERMATOLOGICAL USE OF 7-HYDROXYLATED STEROIDS IN COMBINATION WITH ELASTIN DERIVED PEPTIDES

(75) Inventors: Thomas F. Mitts, Visalia, CA (US); Lawrence B. Sandberg, Murrieta, CA (US); Philip J. Roos, Loma Linda, CA (US)

(73) Assignee: Connective Tissue Imagineering LLC, Visalia, CA (US)

( * ) Notice: Subject to any disclaimer, the term of this patent is extended or adjusted under 35 U.S.C. 154(b) by 0 days.

(21) Appl. No.: 09/443,631

(22) Filed: Nov. 19, 1999

Related U.S. Application Data

(60) Provisional application No. 60/109,246, filed on Nov. 19, 1998.

(51) Int. Cl.[7] .......................... A61K 38/00; A61K 31/56
(52) U.S. Cl. ............................ 514/16; 514/17; 514/18; 514/2; 514/182; 514/177; 514/178; 424/401
(58) Field of Search ................................ 514/16–18, 2, 514/182, 177, 178, 21; 424/401

(56) References Cited

U.S. PATENT DOCUMENTS

| | | |
|---|---|---|
| 4,118,480 A | 10/1978 | Williams |
| 4,179,333 A * | 12/1979 | Braeumer et al. ......... 435/68.1 |
| 4,323,553 A | 4/1982 | Bouillon et al. |
| 4,327,078 A | 4/1982 | Charlet et al. |
| 4,381,294 A | 4/1983 | Bouillon et al. |
| 4,474,763 A * | 10/1984 | Lubowe ....................... 424/177 |
| 4,591,501 A | 5/1986 | Cioca |
| 4,603,146 A | 7/1986 | Kligman |
| 4,659,740 A | 4/1987 | Usher |
| 4,668,476 A | 5/1987 | Bridgham et al. |
| 4,816,513 A | 3/1989 | Bridgham et al. |
| 4,877,805 A | 10/1989 | Kligman |
| 4,891,227 A | 1/1990 | Thaman et al. |
| 4,891,228 A | 1/1990 | Thaman et al. |
| 4,963,656 A | 10/1990 | Mitani |
| 4,983,382 A | 1/1991 | Wilmott et al. |
| 5,017,691 A | 5/1991 | Lee |
| 5,028,695 A | 7/1991 | Eckmayer et al. |
| 5,079,003 A | 1/1992 | Scaffidi et al. |
| 5,122,536 A | 6/1992 | Perricone |
| 5,140,043 A | 8/1992 | Darr et al. |
| 5,223,420 A | 6/1993 | Rabaud et al. |
| 5,503,825 A | 4/1996 | Lane |
| 5,523,291 A | 6/1996 | Janzen et al. |
| 5,587,396 A | 12/1996 | Smith |
| 5,643,949 A | 7/1997 | Van Scott et al. |
| 5,648,209 A | 7/1997 | Avrameas et al. |
| 5,726,040 A | 3/1998 | Ensley et al. |
| 5,736,537 A | 4/1998 | Gubernick et al. |
| 5,763,433 A * | 6/1998 | Morfin ....................... 514/177 |

(List continued on next page.)

FOREIGN PATENT DOCUMENTS

| | | |
|---|---|---|
| JP | 08/255.594 | 3/1993 |
| WO | WO94/08588 A1 | 4/1994 |
| WO | WO96/35428 A1 | 11/1996 |

OTHER PUBLICATIONS

Heiber, A.D. et al., Detection of Elastin in the Human Fetal Membranes: Prosposed Molecular Basis for Elasticity; Placenta; vol. 18; pp. 301–312; 1997.

(List continued on next page.)

*Primary Examiner*—Shengjun Wang
(74) *Attorney, Agent, or Firm*—Benesch, Friedlander, Coplan & Aronoff, LLP

(57) ABSTRACT

The present invention is directed to a composition and method for enhancing the appearance of skin or tissue. The invention is preferably a combination of elastin-derived peptides and steroidal compounds useful in the treatment of problems associated with deficient elastin or conditions that would benefit from increased elastin.

11 Claims, 2 Drawing Sheets

SKIN ELASTIN DATA

U.S. PATENT DOCUMENTS

| | | |
|---|---|---|
| 5,770,697 A | 6/1998 | Ferrari et al. |
| 5,776,441 A | 7/1998 | Scancarella et al. |
| 5,801,192 A | 9/1998 | Dumas et al. |
| 5,945,409 A | 8/1999 | Crandall |
| 5,948,418 A | 9/1999 | Maes et al. |
| 6,025,347 A | 2/2000 | Gubernick et al. |
| 6,069,129 A * | 5/2000 | Sandberg et al. ............ 514/16 |

OTHER PUBLICATIONS

Gibson, M.A. et al., Further Characterization o fProteins Associated with Elastic Fibre Microfibrils Including the Molecular Cloning of MAGP–2 (MP25); The Journal of Biological Chemistry; vol. 271, No. 2 pp. 1096–1103; Jan. 12, 1996.

Price, L.S.C. et al., Valyl–Alanyl–Prolyl–Glycine (VAPG) Sreves as a Quantatative Marker for Human Elastins; Matrix; vol. 13 pp. 307–311; 1993.

Blankenship, J.W. et al., Oxysterol Incorporation Into Rat Aorta Resulting in Elastin Compositional Changes; Lipids; vol. 26, No. 5; pp. 381–384; 1991.

Sandberg, L.B. et al., Quantitation of Elastin in Tissues and Culture: Problems Related to the Accurate Measurement of Small Amounts of Elastin With Special Emphasis on the Rat; Connective Tissue Research; vol. 25, pp. 139–148; 1990.

Sandberg, L.B. et al., Structural Guidelines for an Acceptable Elastin an Tropoelastin: Application Towards Quantitation of Elastin Accumulation in Tissue Culture; Elastin: Chemical and Biological Aspects (Reprinted); pp. 22–44; 1009.

Sandberg, L.B. et al., Quantitation of Elastin Through Measurement of Its Pentapeptide Content; Biochemical and Biophysical Research Communications; vol. 136, No. 2 pp. 672–678; Apr. 29, 1986.

Database CaPlus, AN 108:167920. Bayer et al. Z. Naturforsch., C: Biosci, 42(4), 455–60), Apr. 1987.

Hunninghake et al. Science, 212, 925–927, May 1981.

Database Caplus, DN 127:219499. Morrelli et al. J. Pept. Res., 49 (6), 429–499, Jun. 1997.

Database Caplus, DN 122:102414. Bisaccia et al. Int, J. Pept. Res, 44, 332–341, Apr. 1994.

Database CAPLUS, AN 115:65185, Doi, R. et al., Effects of synthetic human pancreastatin on pancreatic secretion an dblood flow in rats and dogs. Peptides. 1991, vol. 12(3), pp. 449–502.

Database CAPLUS, AN 107:54378, Raju, K. et al., Primary structure of bovine elastin a, b, and c deduced from the sequence of cDNA clones. J. Biol. Chem., 1987, 262(12), pp. 5755–5762.

Database CAPLUS, AN 107:191131, Charten et al. QSAR for peptide bioactivities. Further studies. Pharmacochem. Libr. 1987, vol. 10, pp. 285–290.

Database, CAPULS, 129:187343, Lograno, M. et al., Identification of elastin peptides with vasorelaxant activity on rat thoracic aorta. Int. J. Biochem. Cell Biol., 1998, vol. 30 pp. 497–503.

Ferrance, J., Examiner's first report on patent application No. 30854/99 by Connective Tissue Imagineering LLC, 2001.

* cited by examiner

SEQUENCE LISTING

```
<160> NUMBER OF SEQ ID NOS: 41

<210> SEQ ID NO 1
<211> LENGTH: 3
<212> TYPE: PRT
<213> ORGANISM: mammalian

<400> SEQUENCE: 1

Ala Val Gly
  1

<210> SEQ ID NO 2
<211> LENGTH: 4
<212> TYPE: PRT
<213> ORGANISM: mammalian

<400> SEQUENCE: 2

Val Gly Ala Gly
  1

<210> SEQ ID NO 3
<211> LENGTH: 3
<212> TYPE: PRT
<213> ORGANISM: mammalian

<400> SEQUENCE: 3

Ile Gly Gly
  1

<210> SEQ ID NO 4
<211> LENGTH: 2
<212> TYPE: PRT
<213> ORGANISM: mammalian

<400> SEQUENCE: 4

Leu Gly
  1

<210> SEQ ID NO 5
<211> LENGTH: 4
<212> TYPE: PRT
<213> ORGANISM: mammalian

<400> SEQUENCE: 5

Ile Gly Ala Gly
  1

<210> SEQ ID NO 6
<211> LENGTH: 3
<212> TYPE: PRT
<213> ORGANISM: mammalian

<400> SEQUENCE: 6

Leu Gly Gly
  1
```

```
<210> SEQ ID NO 7
<211> LENGTH: 4
<212> TYPE: PRT
<213> ORGANISM: mammalian

<400> SEQUENCE: 7

Val Ala Pro Gly
  1

<210> SEQ ID NO 8
<211> LENGTH: 4
<212> TYPE: PRT
<213> ORGANISM: mammalian

<400> SEQUENCE: 8

Leu Gly Pro Gly
  1

<210> SEQ ID NO 9
<211> LENGTH: 4
<212> TYPE: PRT
<213> ORGANISM: mammalian

<400> SEQUENCE: 9

Leu Gly Ala Gly
  1

<210> SEQ ID NO 10
<211> LENGTH: 4
<212> TYPE: PRT
<213> ORGANISM: mammalian

<400> SEQUENCE: 10

Val Gly Pro Gly
  1

<210> SEQ ID NO 11
<211> LENGTH: 4
<212> TYPE: PRT
<213> ORGANISM: mammalian

<400> SEQUENCE: 11

Phe Gly Pro Gly
  1

<210> SEQ ID NO 12
<211> LENGTH: 4
<212> TYPE: PRT
<213> ORGANISM: mammalian

<400> SEQUENCE: 12

Val Gly Pro Gln
  1

<210> SEQ ID NO 13
<211> LENGTH: 3
<212> TYPE: PRT
<213> ORGANISM: mammalian

<400> SEQUENCE: 13

Leu Gly Ala
  1

<210> SEQ ID NO 14
```

```
<211> LENGTH: 4
<212> TYPE: PRT
<213> ORGANISM: mammalian

<400> SEQUENCE: 14

Val Gly Pro Ala
  1

<210> SEQ ID NO 15
<211> LENGTH: 4
<212> TYPE: PRT
<213> ORGANISM: mammalian

<400> SEQUENCE: 15

Val Val Pro Gly
  1

<210> SEQ ID NO 16
<211> LENGTH: 4
<212> TYPE: PRT
<213> ORGANISM: mammalian

<400> SEQUENCE: 16

Ala Val Pro Gly
  1

<210> SEQ ID NO 17
<211> LENGTH: 4
<212> TYPE: PRT
<213> ORGANISM: mammalian

<400> SEQUENCE: 17

Val Val Pro Gln
  1

<210> SEQ ID NO 18
<211> LENGTH: 6
<212> TYPE: PRT
<213> ORGANISM: mammalian

<400> SEQUENCE: 18

Val Ala Ala Arg Pro Gly
  1               5

<210> SEQ ID NO 19
<211> LENGTH: 7
<212> TYPE: PRT
<213> ORGANISM: mammalian

<400> SEQUENCE: 19

Leu Gly Ala Gly Gly Ala Gly
  1               5

<210> SEQ ID NO 20
<211> LENGTH: 4
<212> TYPE: PRT
<213> ORGANISM: mammalian

<400> SEQUENCE: 20

Ala Ile Pro Gly
  1

<210> SEQ ID NO 21
<211> LENGTH: 5
<212> TYPE: PRT
```

```
<213> ORGANISM: mammalian

<400> SEQUENCE: 21

Leu Gly Pro Gly Gly
 1               5

<210> SEQ ID NO 22
<211> LENGTH: 5
<212> TYPE: PRT
<213> ORGANISM: mammalian

<400> SEQUENCE: 22

Ala Ala Ala Gln Ala
 1               5

<210> SEQ ID NO 23
<211> LENGTH: 5
<212> TYPE: PRT
<213> ORGANISM: mammalian
<220> FEATURE:
<221> NAME/KEY: MOD_RES
<222> LOCATION: (4)

<400> SEQUENCE: 23

Val Gly Val Xaa Gly
 1               5

<210> SEQ ID NO 24
<211> LENGTH: 5
<212> TYPE: PRT
<213> ORGANISM: mammalian

<400> SEQUENCE: 24

Val Tyr Pro Gly Gly
 1               5

<210> SEQ ID NO 25
<211> LENGTH: 6
<212> TYPE: PRT
<213> ORGANISM: mammalian

<400> SEQUENCE: 25

Ile Gly Gly Val Gly Gly
 1               5

<210> SEQ ID NO 26
<211> LENGTH: 6
<212> TYPE: PRT
<213> ORGANISM: mammalian

<400> SEQUENCE: 26

Val Ala Pro Gly Val Gly
 1               5

<210> SEQ ID NO 27
<211> LENGTH: 5
<212> TYPE: PRT
<213> ORGANISM: mammalian

<400> SEQUENCE: 27

Leu Gly Val Gly Gly
 1               5

<210> SEQ ID NO 28
<211> LENGTH: 4
```

```
<212> TYPE: PRT
<213> ORGANISM: mammalian

<400> SEQUENCE: 28

Val Leu Pro Gly
 1

<210> SEQ ID NO 29
<211> LENGTH: 5
<212> TYPE: PRT
<213> ORGANISM: mammalian

<400> SEQUENCE: 29

Phe Arg Ala Ala Ala
 1               5

<210> SEQ ID NO 30
<211> LENGTH: 6
<212> TYPE: PRT
<213> ORGANISM: mammalian

<400> SEQUENCE: 30

Val Gly Gly Val Pro Gly
 1               5

<210> SEQ ID NO 31
<211> LENGTH: 5
<212> TYPE: PRT
<213> ORGANISM: mammalian

<400> SEQUENCE: 31

Phe Gly Pro Gly Gly
 1               5

<210> SEQ ID NO 32
<211> LENGTH: 5
<212> TYPE: PRT
<213> ORGANISM: mammalian

<400> SEQUENCE: 32

Val Gly Val Pro Gly
 1               5

<210> SEQ ID NO 33
<211> LENGTH: 6
<212> TYPE: PRT
<213> ORGANISM: mammalian

<400> SEQUENCE: 33

Val Leu Pro Gly Ala Gly
 1               5

<210> SEQ ID NO 34
<211> LENGTH: 5
<212> TYPE: PRT
<213> ORGANISM: mammalian
<220> FEATURE:
<221> NAME/KEY: MOD_RES
<222> LOCATION: (4)

<400> SEQUENCE: 34

Val Gly Leu Xaa Gly
 1               5

<210> SEQ ID NO 35
```

```
<211> LENGTH: 5
<212> TYPE: PRT
<213> ORGANISM: mammalian

<400> SEQUENCE: 35

Leu Gly Val Gly Ala
 1               5

<210> SEQ ID NO 36
<211> LENGTH: 4
<212> TYPE: PRT
<213> ORGANISM: mammalian

<400> SEQUENCE: 36

Ala Phe Pro Gly
 1

<210> SEQ ID NO 37
<211> LENGTH: 5
<212> TYPE: PRT
<213> ORGANISM: mammalian

<400> SEQUENCE: 37

Ala Phe Pro Gly Ala
 1               5

<210> SEQ ID NO 38
<211> LENGTH: 5
<212> TYPE: PRT
<213> ORGANISM: mammalian

<400> SEQUENCE: 38

Val Gly Ile Pro Ala
 1               5

<210> SEQ ID NO 39
<211> LENGTH: 6
<212> TYPE: PRT
<213> ORGANISM: mammalian

<400> SEQUENCE: 39

Val Gly Gly Ile Pro Thr
 1               5

<210> SEQ ID NO 40
<211> LENGTH: 7
<212> TYPE: PRT
<213> ORGANISM: mammalian

<400> SEQUENCE: 40

Val Gly Val Gly Val Pro Gly
 1               5

<210> SEQ ID NO 41
<211> LENGTH: 6
<212> TYPE: PRT
<213> ORGANISM: mammalian

<400> SEQUENCE: 41

Leu Gly Pro Gly Val Gly
 1               5
```

COSMETIC OR DERMATOLOGICAL USE OF 7-HYDROXYLATED STEROIDS IN COMBINATION WITH ELASTIN DERIVED PEPTIDES

CROSS-REFERENCE TO RELATED APPLICATION

This application claims the benefit of U.S. Provisional Application No. 60/109,246, filed Nov. 19, 1998.

BACKGROUND OF THE INVENTION

1. Field of the Invention

The present invention relates generally to a composition which is therapeutic and/or cosmetic to the tissue to which it is applied. The composition of the present invention preferably modifies or appears to modify the physical characteristics of the tissue to which it is applied, and the tissue being modified is preferably mammalian skin tissue. The present invention relates generally to the use of 7-hydroxylated steroids in such compositions useful in prevention and/or to treating the effects of aging and of the action of ultra-violet radiation (UV) on the skin. In an alternative embodiment of the present invention, the invention may include peptides which are formulated at therapeutically effective concentrations to increase the appearance skin. The peptides are preferably soluble in an aqueous solution, and more preferably are comprised of small peptides (usually less than about 10 amino acids in length). It has been found that the most preferred peptides are ones which correspond to or are homologous with portions of elastin, particularly with peptides which correspond to or are homologous with portions of elastin endogenous to the tissue being treated. Accordingly, it has been found that digestion of elastin, for example hydrolytic or site specific enzymatic cleavage of elastin results in peptides which are particularly suitable for use in the present invention. Accordingly, the peptides which result from digesting can be used directly in the therapeutic formulation of the present invention or may be analyzed and sequenced and synthesized by those methods known in the art (i.e. solid state, liquid, and over expression). As used herein, the term "peptide" is not meant to convey any meaning regarding the precursor material or methods utilized to synthesize or make the peptides. Additionally; the term "elastin peptide fragment" in either singular or plural form refers to the fact that the peptide or amino acid sequence being discussed corresponds to, is the biological equivalent of, or is homologous with, a portion of elastin, more specifically to a portion or fragment of elastin endogenous to the animal being treated. However, the term "elastin peptide fragment" is not meant to convey any meaning regarding the source or starting material or method of use to make the elastin peptide fragment. As stated above, peptides of the present invention are preferably formed by enzymatic cleavage of elastin and are even more preferably formed by cleavage of elastin with thermolysin to form hydrophilic elastin derived peptides. It is also preferable that the peptides of the present invention are at a therapeutically effective concentration within the therapeutic or cosmetic composition, wherein the therapeutically effective concentration is in a range of about 0.0002% to about 90% by weight of peptide, more preferably in a range of about 0.05% to about 50% peptide, even more preferably in a range of about 0.5% to about 10% peptide, even more preferably about 1.5% peptide, and most preferably about 1.3% hydrolyzed elastin peptide. The therapeutic composition of the present invention can be formulated as a cosmetic preparation to be applied topically to a patient's skin, such as in an emulsion, lotion, spray, powder, ointment, cream, or foam or in other suitable pharmaceutical vehicles or carriers commonly known in the art for other types of administration (i.e., subcutaneous). The delivery system of the present invention is preferably a topical delivery system but also may be a subcutaneous, transcutaneous, oral, nasal, aerosol, or patch delivery system.

2. Background and Description of the Related Art

Skin, in particular mammalian skin consists of a number of overlapping layers of cells. The outermost layer of mammalian skin is called the stratum corneum. This layer protects mammalian skin from physical and atmospheric harm, acting as a barrier to external dangers. The degree of softness or texture of the stratum corneum is directly dependent on its moisture content. However, it has been found that, in the lower layers of the skin, degenerative changes which occur with age are not caused principally by a lack of moisture. Therefore, even though the texture and appearance of the skin is dependent on the moisture content of the skin, other factors have been shown to influence the overall appearance and texture of the skin. For example, it has been found that the loss of elasticity in the skin decreases the tone and turgor of the skin. It is speculated that the decrease in skin tone and turgor occurs through degradation of certain complex polypeptides which are present in the skin. These complex polypeptides include elastin and collagen, among others.

Elastin is a highly cross-linked complex polypeptide and is a major component of elastic fibers present in the skin and connective tissue of animals. Elastin appears to be primarily responsible for the physiological elasticity of tissue. In normal mammalian skin, specifically human skin, elastic tissue proteins represent a relatively small fraction of the total dermal proteins, but play a very important role in maintaining or improving the skin tone and structure. Elastin itself is the main protein substance present in elastic fibers and occurs in tendons, blood vessels, and connective tissue. When isolated from these sources, it is normally in the form of a brittle, fibrous, yellowish material which is insoluble in water, alcohol and ether but is somewhat soluble in concentrated aqueous alkali metal hydroxide solutions. The dense cross-linked structure of elastin makes it very difficult to solubilize. There have been many attempts to solubilize elastin and create cosmetic agents from the solubilized elastin. To date, these techniques have not found a large degree of commercial success. Attempts to solubilize are described for example in a U.S. Pat. No. 4,327,078. However, it has been found that elastin is only slightly absorbed by the skin and does not sufficiently penetrate the skin to produce substantial benefits to the skin.

The formation of steroidal hormones, their interrelations and their functions have been widely described. The functions of pregnenolone (PREG) and of dehydroepiandrosterone (DHEA) as well as certain of their derivatives have been described in the International Published Application No. WO 94/08588, the teachings of which are hereby incorporated herein by reference thereto in its entirety.

Dihydroepiandrosterone and its sulphate derivative (S-DHEA) circulate in large quantities in humans, but its level reduces with age. It has thus been proposed to use S-DHEA in a cosmetic composition for topical application intended to treat certain signs of aging. The many effects of DHEA have been described, and certain of them oppose the processes and pathologies associated with aging. Despite numerous experiments, no completely satisfactory explanations for the effects of DHEA have been put forth, and the therapeutic use of DHEA has revealed undesirable secondary effects, particularly for women, as a potential precursor of androgynous hormones.

It has been shown that the 7-hydroxylated derivatives of PREG and of DHEA are formed by an enzyme system present in many tissues and organs, including the skin where they encourage mechanisms associated with immunity. Just like the amounts of DHEA circulating, the activity of these hydroxylating enzymes reduces with age.

Recent work relating to the cutaneous modifications caused by age or by UV and their medical treatment specifically considers retinoic acid, the α-hydroxy acids and DHEA, but does not consider 7-hydroxysteroids.

The production of 7-hydroxylated derivatives of DHEA has been known for a long time in the tissues of the human fetus, in the amniotic epithelium, the human liver, the testicles and human epididymus and in the human pre-adipocytes. For the purposes of the present invention, it is preferable that the 7α-hydroxylated derivatives of DHEA be isolated by the above-identified sources, even more preferable that the derivatives of DHEA be selectively 7-hydroxylated (7α-hydroxylated) by *Fusarium moniliforme*. Furthermore, the amounts of 7α-hydroxy-DHEA in circulation in pre-menopausal women have been measured at 200–300 pg/ml, and 3β, 7α dihydroxy-5α-androstan-17-one (7α-hydroxy-isoandrosterone) has been identified in human urine. More recently, the phenomenon of 7-hydroxylation has been extended to other steroids that have, as does DHEA, a 3β-hydroxylated structure (e.g. PREG, 5α-androstane-3β, 17β-diol, 3β-hydroxy-5α-androstan-17-one and 3β-hydroxy-5α-pregnan-20-one).

Work on 7-hydroxylated steroids has proved that they are devoid of the distinctive hormonal effects of either androgens or estrogens or of effects on the secretion of hypophysial hormones. These results taken together have lead to the 7-hydroxylation of steroids being considered as a terminal hormonal deactivation process that leads to the urinary and biliary excretion of the 7-hydroxylated steroid products. It is only very recently that it has been possible to explain, in part, the many effects observed with DHEA by the immunostimulatory properties of its 7-hydroxylated derivatives. The antiglucocorticoidal properties shown by the 7α- and the 7β-hydroxy-DHEA have been proven and extended to other 7-hydroxylated steroids, such as those described in the International Publications Nos. WO 93/20687 and WO 94/08588, the teachings of which are herein incorporated by reference as if set forth in their entireties herein, for their role in triggering immune processes.

It appears that DHEA and the production of its 7-hydroxylated derivatives reduce with age. During aging, the supply of hormonal steroids to the skin is therefore modified with a predominance of glucocorticoids the effects of which as promoters of cutaneous aging are known.

Consequently, a localized supply of 7-hydroxylated steroids endowed with a particular antiglucocorticoid effect and yet natural allows the treated skin to be restored within its young age steroidal context.

The effects of 7-hydroxylated steroids and their derivatives on the cells that constitute the human skin and which are affected during aging or after UV irradiation were studied. Evidence was found that the effects of glucocorticoids leading to cellular apoptosis are obstructed by 7-hydroxylated steroids and that their action on the cutaneous cells is translated into beneficial and protective effects.

In a surprising way, the results obtained with the compounds of the invention do not correspond to those classically expected with steroidal hormones. In effect, the process of hydroxylation carried out by the body on PREG and DHEA is irreversible and due to this fact, the classic steroidal hormones can no longer be produced from the 7-hydroxylated derivatives.

As a consequence, the use of 7-hydroxysteroids for cosmetic purposes to treat or to prevent the cutaneous effects of aging has remarkable advantages compared with previously known steroids of the previously known cosmetic compositions.

SUMMARY OF THE PRESENT INVENTION

The present invention is further directed to a composition for improving tissue texture, wherein the composition includes an elastin peptide which is synthesized by selectively cleaving elastin. Preferably the composition includes a pharmaceutical delivery system and the elastin is derived from animal tissue. More preferably, ligamentum nuchea is the source of the elastin starting material used in the present invention. The elastin of the present invention is preferably selectively cleaved by enzymatic digestion of the elastin with thermolysin.

The present invention is further directed to a method of enhancing the functionality, tone, turgor, and elasticity of the tissue to which it is administered. With particularity to skin tissue, the appearance of the skin is enhanced as a consequence of improving the elasticity of the tissue to which the composition is applied. In one embodiment it is most preferable that the method include the step of stimulating endogenous production of elastin in the patient to which an elastin fragment peptide is being applied. It is preferable that the administration step be comprised of a number of separate administration steps which are repeated most preferably twice daily over a predetermined time, wherein the predetermined time exceeds one week of daily administration of the composition, more preferably two weeks, and most preferably at least a month of daily topical application (with twice daily of the composition administration over the month being even more preferable.). As with the composition of the present invention, in the method of the present invention, it is preferable that the elastin peptide fragment be comprised of peptides having a molecular weight of less than about 10,000 Da, more preferably 90% of the peptides have a molecular weight of less than about 10,000 Da. It is even more preferable that the elastin peptide fragment be comprised of peptides having a molecular weight of less than about 3,000 Da and most preferably less than about 1,000 Da. In fact, it has been found that the preferred molecular weight range of peptides utilized in the present invention is in the range of about 100–1,000 Da; more preferred about 150–800 Da; even more preferred about 180–600 Da; and most preferably the therapeutic or cosmetic composition includes peptides having a molecular weight in the range of about 188–585 Da.

It has also been found that the peptides which best accomplish an increase in tissue elasticity and turgor are ones which correspond to or are homologous with portions of elastin, particularly with peptides which correspond to or are homologous with portions of elastin endogenous to the tissue being treated. Accordingly, it has been found that digestion of elastin, for example hydrolytic or site specific enzymatic cleavage of the elastin results in peptides which are particularly suitable for use in the present invention. Accordingly, the peptides which result from digesting can be used directly in the therapeutic formulation of the present invention or may be analyzed and sequenced and synthesized by those methods known in the art (i.e. solid state, liquid, and over expression). As used herein, the term "peptide" is not meant to convey any meaning regarding the precursor material or methods utilized to synthesize or make the peptides. Additionally, the term "elastin peptide fragment" in either singular or plural form refers to the fact that the peptide or amino acid sequence being discussed corresponds to, is the biological equivalent of, or is homologous with, a portion of elastin, more specifically to a portion or fragment of elastin endogenous to the animal being treated. However, the term "elastin peptide fragment" is not meant to convey any meaning regarding the source or starting material or method of use to make the elastin peptide fragment. As stated above, peptides of the present invention are preferably formed by enzymatic cleavage of elastin and are even more preferably formed by cleavage of elastin with thermolysin to form hydrophilic elastin derived peptides. It is also preferable that the peptides of the present invention are at a therapeutically effective concentration within the therapeutic or cosmetic composition, wherein the therapeutically effective concentration is in a range of about 0.0002% to about 90% by weight of peptide, more preferably in a range of about 0.05% to about 50% peptide, even more preferably in a range of about 0.5% to about 10% peptide, even more preferably about 1.5% peptide, and most preferably about 1.3% hydrolyzed elastin peptide. The therapeutic composition of the present invention can be formulated as a cosmetic preparation to be applied topically to a patient's skin, such as in an emulsion, lotion, spray, powder, ointment, cream, or foam or in other suitable pharmaceutical vehicles or carriers commonly known in the art for other types of administration (i.e., subcutaneous). The delivery system of the present invention is preferably a topical delivery system but also may be a subcutaneous, transcutaneous, oral, nasal, aerosol, or patch delivery system.

The present invention is further directed to a composition for improving tissue texture, wherein the composition is comprised of an elastin peptide which is synthesized by selectively cleaving elastin. Preferably the composition includes a pharmaceutical delivery system and the elastin is derived from animal tissue. More preferably, ligamentum nuchea is the source of the elastin starting material used in the present invention. The elastin of the present invention is preferably selectively cleaved by enzymatic digestion of the elastin with thermolysin. This thermolytic cleavage preferably results in a elastin peptide fragment or fragments having a molecular weight of less than about 10,000 Da, more preferably less than about 3,000 Da, even more preferably less than about 1,000 Da. A preferred composition of the present invention is one in which the elastin peptide fragment or fragments have a molecular weight of less than 1,000 Da. It is also preferable that the elastin peptides fragment or fragments include a sequence according to the formula of $R_1$-Prolyl-Glycine-$R_2$, wherein $R_1$ is an amino acid or amino acid sequence (peptide) which is at the amino terminal and $R_2$ is an amino acid or amino acid sequence (peptide) which is at the carboxyl terminal.

BRIEF DESCRIPTION OF THE DRAWINGS

The features, aspects, and advantages of the present invention will become better understood with regard to the following description, appended claims, and accompanying drawings where:

DETAILED DESCRIPTION OF THE PREFERRED EMBODIMENT

Figure 1:
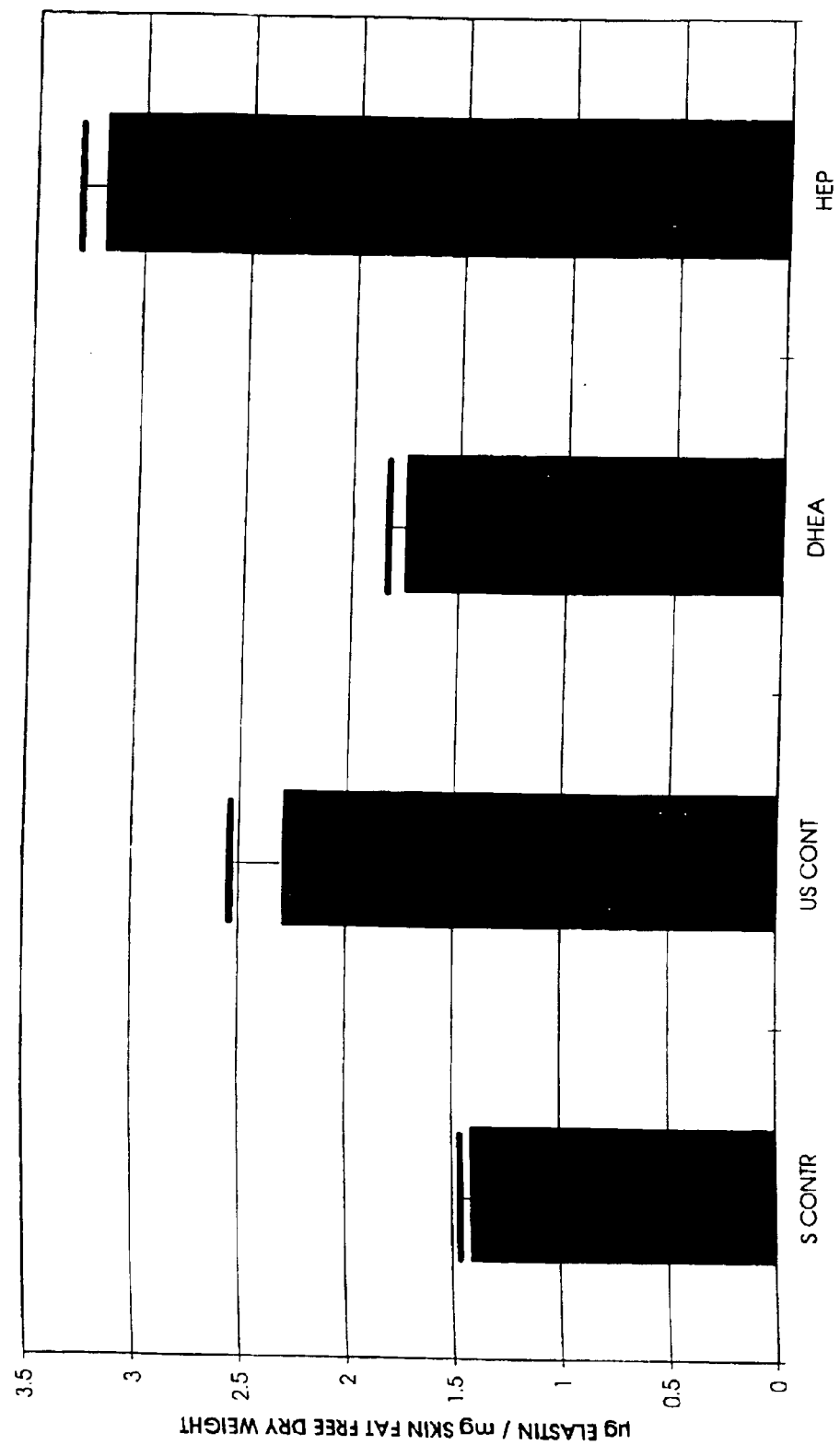
FIG. 1 is a bar graph illustrating increased elastin production as a result of application of the present invention to mammalian skin.

In order that the invention herein described may be more fully understood, the following detailed description is set forth. The present invention relates to composition which is useful in increasing the elasticity of tissue. The present invention is also directed to administering therapeutically effective concentrations of the composition to the tissue in need thereof.

As used herein, the term "subject" or "patient" means any mammal, including humans, in which elastin is utilized for proper tissue function. The methods herein for use contemplate prophylactic use as well as curative use in therapy of an existing condition.

As used herein, the term "about" means plus or minus 10% of the numerical value of the number with which it is being used. Therefore, about 50% means in the range of 45%–55%. As used herein, the term "Dalton" (or "Da") refers to the unit of mass which is equivalent to the mass of a hydrogen atom ($1.66 \times 10^{-24}$ gram). Generally speaking, the term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity. Unless otherwise indicated, the term "skin" means that outer integument or covering of the body, consisting of the dermis and the epidermis and resting upon subcutaneous tissue.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with elastin peptide fragment, can include, but is not limited to, providing an elastin peptide fragment into or onto the target tissue; providing an elastin peptide fragment systemically to a patient by, e.g., intravenous injection whereby the therapeutic reaches the target tissue; providing an elastin peptide fragment in the form of the encoding sequence thereof to the target tissue (e.g., by so-called gene-therapy techniques) whereby the elastin peptide fragment is expressed within the target tissue.

Details on techniques for formulation and administration of pharmaceuticals may be found in the latest edition of *Remington's Pharmaceutical Sciences* (Mack Publishing Co, Easton Pa.). Although local topical delivery is desirable, there are other means of delivery, for example: oral, parenteral, aerosol, intramuscular, subcutaneous, transcutaneous, intamedullary, intrathecal, intraventricular, intravenous, intraperitoneal, or intranasal administration.

As used herein, the term "therapeutic" means an agent utilized to treat, combat, ameliorate, prevent or improve an unwanted condition or disease of a patient. The condition being treated in the present invention is deficient elastin in tissue, that is, a need in the tissue for more elastin: As it applies to skin, it is measured by turgor, tone, appearance, degree of wrinkles, and youthfulness. As the term applies to blood vessels it may be measured by the degree of elasticity or proper vasomotor response (vasodilatation/vasoconstriction) of the vessel. Accordingly, therapeutic treatment of blood vessels may have implications in diseases associated with visco-elasticity, including hypertension, arteriosclerosis, angina, angiogenesis, myocardial infarction, coronary thrombosis, restenosis post angioplasty, and chronic obstructive pulmonary disease.

Finally, the term "cosmetic," as used herein, refers to a beautifying substance or preparation which preserves, restores, bestows, simulates, or enhances the appearance of bodily beauty, specifically as it relates to the appearance of tissue or skin.

As stated above, the present invention is directed to an elastin peptide fragment which is useful as a therapeutic and or cosmetic composition or agent for modifying tissue, especially skin. The term "modify" is used to convey that the present invention changes either the appearance, form, characteristics and/or the physical attributes of the tissue to which it is being provided, applied or administered. The change in form can be reflected in any of the following alone or in combination: enhanced appearance of the skin; increased softness of the skin; increased turgor of the skin; increased texture of the skin; increased elasticity of the skin; decreased wrinkle formation and increased endogenous elastin production in the skin.

The source of the starting elastin material can derive from a number of sources known in the art. It is known, for example, that the ligamentum nuchae is made up largely of elastin, with only a relatively small amount of collagen. More than 70% of the dry weight of this ligament is elastin. Due to the relatively high elastin content and relatively low collagen content of ligamentum nuchae, it is an ideal starting material to use in deriving the elastin peptide fragments of the present invention. In a preferred embodiment of the present invention, ligamentum nuchae is utilized. It may be preferable to clean the ligamentum nuchae first using a procedure similar to that disclosed in U.S. Pat. No. 5,028,695, which this portion of is incorporated herein by reference hereto. Although the preferred source of the starting material of the present invention is ligamentum nuchae, other ligaments, tendons, connective tissue, tissue, and synthetic sources may also be used. For example, the arteries and lungs, and other animal tissue, especially those which have significant amounts of elastin, can be used. Also, elastin from different sources, or elastin and collagen from the same or different sources could be mixed together to produce a particular advantageous mix suitable for an intended use. For example, rat, sheep, and porcine aorta can be used as a source of elastin as described in L. B. Sandberg, *Connective Tissue Research*, 1990, Vol. 25, pp. 139–148, which is hereby incorporated herein in its entirety by reference hereto.

In the present invention, the ligament extraction is comprised of taking dissected ligamentum nuchae ligaments and removing as much fat and excess connective tissue as possible. These "clean" ligaments are then chopped into about one centimeter square (1 cm$^2$) pieces and washed with doubly distilled water ("DDW"). The clean ligaments are then placed on a metal mortar, pre-chilled to −20° F. and liquid nitrogen is added to freeze the tissue. The ligaments are then minced or pulverized with the appropriate tool and re-suspended in 1% aqueous NaCl at a ratio of about 100 grams of tissue to about three liters of 1% aqueous NaCl and homogenized in a Waring blender at high speed for 30–60 seconds. The homogenized ligament is transferred to a four-liter beaker and stirred overnight at 4° C. on a magnetic stirrer, after which it is centrifuged at 32,500×G and the supernatant is checked for protein content using the Biuret method for protein determination. The Biuret reaction is done by mixing 2 milliliters of extract with 3 milliliters of reagent and reading immediately either by simple visual inspection or at 540 nanometers on a spectrophotometer to determine the protein concentration of the supernatant. The supernatant is then discarded. The pellet (referred to hereinafter as the elastin pellet) is resuspended in 1% aqueous NaCl and homogenized. The process of homogenizing in a Waring blender, stirring overnight and centrifuging are repeated three to four times until the supernatant is Biuret negative. After centrifugation, the elastin pellet is resuspended in DDW and autoclaved 30 psi for six hours. The resuspended elastin pellet is centrifuged again and the supernatant is tested for protein content via the Biuret method. The elastin is washed with boiling DDW and then with DDW at room temperature and the washes are tested for protein content via the Biuret method. If the washes are Biuret negative, the elastin pellet is dried with chloroform/methanol solution at a ratio of 2 parts chloroform to 1 part methanol. If the Biuret test is positive, the six hour autoclave procedure with wash step is repeated until the Biuret test is negative. Finally, the elastin residue is washed with five volumes of pure methanol and air-dried at room temperature. The elastin residue is transferred to a desiccator and dried over $P_2O_5$ for 24 hours until the weight of the elastin residue is stable. The elastin residue is then milled in a Willey mill through a 40-mesh screen followed by a 60-mesh screen.

For the thermolysin digestion, three times re-crystallized thermolysin product from CalBiochem (10394 Pacific Center Court, San Diego, Calif. 92121) is used. The thermolysin preparation contains sufficient calcium to ensure maximal activity of the enzyme. The thermolysin digestion is done as follows: a waterbath is brought to a 55° C. temperature with a rotary shaker and five grams of the finely milled largely insoluble elastin residue is hydrated with one liter of DDW for fifteen minutes at room temperature. After hydration, the one liter DDW which contains the five grams of elastin is placed in the 55° C. bath and the pH of the elastin/water mixture is brought to a pH between 7–8 with 10% methylamine. Fifty milligrams of thermolysin (*bacillus thermoproleolyticus*) is added directly to the elastin water mixture. The thermolysin contains about 60% protein (60.2%), about 13% (13.2%) sodium acetate, and about 25% (25.3%) calcium acetate, with a specific activity of about 8.720 I.U./mg dry weight. The pH of the elastin water mixture is monitored with a pH meter or pH stat and adjusted with 10% methylamine to keep the pH between 6.8 and 7.5. The digestion is allowed to continue for 75 minutes and then concentrated hydrochloric acid is added to adjust the pH to 3.0 to terminate the digestion.

After digestion is terminated, the digested product is filtered through a PM 10 Diaflow 10,000 molecular weight cut-off ultra-filtration membrane to filter out any-protein or peptides exceeding about 10,000 Da molecular weight. The resulting supernatant is an elastin-derived composition comprised of peptides having a molecular weight of less than about 10,000 Da. As it turns out, the most preferred composition is comprised of an elastin peptide fragment with a molecular weight of less than about 1,000 Da. Table 1 is a list of peptide sequences isolated from the thermolytic cleavage of elastin. These isolated fractions, either alone or in combination, when applied to tissue, result in the tissue, specifically mammalian skin, exhibiting characteristics of increased skin elasticity, including skin softness and increased turgor as well as an overall increase in the attractiveness of the skin. As can be seen from Table 1 below, it is preferable that the composition of the present invention be comprised of elastin peptide fragments having an amino acid chain length of less than about 10 amino acids or having a molecular weight in the range of about 150–800 Da, even more preferably about 180 Da to about 600 Da, and most preferably from about 188 Da to about 585 Da. It is also preferable that the peptide or peptides used in formulating the composition of the present invention are comprised substantially of amino acids having an apolar and/or an uncharged side group (i.e. alanine, valine, proline, glycine), more preferably comprised of peptides which include glycine or proline, and even more preferably comprised of peptides containing glycine and proline in each amino acid sequence.

The elastin peptide fragments which have been identified as being particularly useful in the present invention have the following amino acid sequences:

TABLE 1

| SEQ # | PEPTIDE | MOL WT | NAME (N- to C-terminal) | c-DNA Copies |
|---|---|---|---|---|
| 1. | AVG | 245 | Alanine-Valine-Glycine | 1 |
| 2. | VGAG | 302 | Valine-Glycine-Alanine-Glycine | 2 |
| 3. | IGG | 302 | Isoleucine-Glycine-Glycine | 4 |
| 4. | LG | 188 | Leucine-Glycine | 26 |
| 5. | IGAG | 316 | Isoleucine-Glycine-Alanine-Glycine | 2 |
| 6. | LGG | 245 | Leucine-Glycine-Glycine | 6 |
| 7. | VAPG | 342 | Valine-Alanine-Proline-Glycine | 2 |
| 8. | LGPG | 342 | Leucine-Glycine-Proline-Glycine | 3 |
| 9. | LGAG | 316 | Leucine-Glycine-Alanine-Glycine | 4 |
| 10. | VGPG | 328 | Valine-Glycine-Proline-Glycine | 2 |
| 11. | FGPG | 376 | Phenylalanine-Glycine-Proline-Glycine | 2 |
| 12. | VGPQ | 399 | Valine-Glycine-Proline-Glutamine | 1 |
| 13. | LGA | 259 | Leucine-Glycine-Alanine | 7 |
| 14. | VGPA | 342 | Valine-Glycine-Proline-Alanine | 1 |
| 15. | VVPG | 370 | Valine-Valine-Proline-Glycine | 2 |
| 16. | AVPG | 342 | Alanine-Valine-Proline-Glycine | 2 |
| 17. | VVPQ | 441 | Valine-Valine-Proline-Glutamine | 1 |
| 18. | VAARPG | 569 | Valine-Alanine-Alanine-Arginine-Proline-Glycine | 1 |
| 19. | LGAGGAG | 501 | Leucine-Glycine-Alanine-Glycine-Glycine-Alanine-Glycine | 1 |
| 20. | AIPG | 356 | Alanine-Isoleucine-Proline-Glycine | 2 |
| 21. | LGPGG | 399 | Leucine-Glycine-Proline-Glycine-Glycine | 1 |
| 22. | AAAQA | 430 | Alanine-Alanine-Alanine-Glutamine-Alanine | 1 |
| 23. | VGVHypG | 444 | Valine-Glycine-Valine-Hydroxyproline-Glycine | 14* |
| 24. | VYPGG | 491 | Valine-Tyrosine-Proline-Glycine-Glycine | 1 |
| 25. | IGGVGG | 458 | Isoleucine-Glycine-Glycine-Valine-Glycine-Glycine | 1 |
| 26. | VAPGVG | 498 | Valine-Alanine-Proline-Glycine-Valine-Glycine | 1 |
| 27. | LGVGG | 401 | Leucine-Glycine-Valine-Glycine-Glycine | 3 |
| 28. | VLPG | 384 | Valine-Luecine-Proline-Glycine | 3 |
| 29. | FRAAA | 534 | Phenylalanine-Arginine-Alanine-Alanine-Alanine | 1 |
| 30. | VGGVPG | 484 | Valine-Glycine-Glycine-Valine-Proline-Glycine | 1 |
| 31. | FGPGG | 433 | Phenylalanine-Glycine-Proline-Glycine-Glycine | 1 |
| 32. | VGVPG | 427 | Valine-Glycine-Valine-Proline-Glycine | 14* |
| 33. | VLPGAG | 512 | Valine-Leucine-Proline-Glycine-Alanine-Glycine | 1 |
| 34. | VGLHypG | 458 | Valine-Glycine-Leucine-Hydroxyproline-Glycine | 1** |
| 35. | LGVGA | 415 | Leucine-Glycine-Valine-Glycine-Alanine | 1 |
| 36. | AFPG | 390 | Alanine-Phenylalanine-Proline-Glycine | 1 |

TABLE 1-continued

| SEQ # | PEPTIDE | MOL WT | NAME (N- to C-terminal) | c-DNA Copies |
|---|---|---|---|---|
| 37. | AFPGA | 461 | Alanine-Phenylalanine-Proline-Glycine-Alanine | 1 |
| 38. | VGIPA | 455 | Valine-Glycine-Isoleucine-Proline-Alanine | 1 |
| 39. | VGGIPT | 542 | Valine-Glycine-Glycine-Isoleucine-Proline-Threonine | no |
| 40. | VGVGVPG | 583 | Valine-Glycine-Valine-Glycine-Valine-Proline-Glycine | 2 |
| 41. | LGPGVG | 498 | Leucine-Glycine-Proline-Glycine-Valine-Glycine | 1 |

*Sequence Nos. 23 and 32 appear to be a common sequence because Proline hydroxylation is a post-translational event.
**as VGLPG.

It should be noted that the above sequences account for about 40% of all the elastin sequences with the rest of the sequences being reduced to free amino acids or desmosine crosslinks and that these amino acids are not being accounted for with sequencing.

The elastin peptide fragment/water mixture which is obtained upon digestion with thermolysin described is preferably flash evaporated to dryness and redissolved in a small volume of DDW and if desired is diluted sufficiently with DDW for lyophilization to dryness. In the alternative, rather than redissolving the hydrophilic elastin peptide, the filtered product is freeze dried twice, resulting in a powder which contains 30 weight chemically-bound water and very little salt (NaCl). Preferably the powder for therapeutic use is dissolved to a concentration of about 0.0002% to about 90% by weight of elastin peptide fragment, more preferably in a range of about 0.05% to about 50%, even more preferably in a range of about 0.05% to about 10% elastin peptide fragment, and more preferably about 1.5% elastin peptide fragment, and most preferably about 1.3% peptide fragment or fragments in a vehicle which is suitable for topical or subcutaneous administration.

As can be seen from FIG. 1, the topical treatment with a composition which included peptide fragments at a concentration of about 1.3% when applied to the skin of a Sprague-Dawley male rat over a one month period illustrates a doubling of the elastin content of the skin, as compared to both control samples and similar applications and concentration of DHEA. In FIG. 1, S CONTR represents the Shaven Control and US CONTR represents the Unshaven Control. FIG. 1 illustrates that the present invention has the advantageous qualities of enhancing the softness or elasticity of the skin by increasing the endogenous production of elastin in the skin. The present invention is also directed to a method of improving the texture of skin, specifically the physical appearance of the skin by improving the endogenous production of elastin. The method of the present invention employs any of a number of known administrative routes such as oral, IV, subcutaneous, transcutaneous, and topical administration. The method of the present invention employs a pharmaceutical or cosmetic composition which enhances the physical appearance of and/or the elasticity of tissue due to increased production of endogenous elastin in the tissue to which the formulation is administered. It is believed that the limit for skin penetration of elastin peptide fragment is a molecular weight of about 20,000 Da. Due to the fact that the present invention uses peptides derived from elastin through thermolytic cleavage which have a molecular weight of less than about 10,000 Da, more preferably less than about 3,000 Da, even more preferably less than 1,000

Da, the peptides meeting this criteria present in the composition of the present invention are absorbed by the skin upon application. Beyond the increased absorption due to the relative small size of the active peptides of the present invention, the peptides themselves which preferably correspond to those formed through thermolytic cleavage of elastin with thermolysin, appear to have increased activity in the production of endogenous elastin on a skin to which the administration or the therapeutic composition is applied.

The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. U.S. Pat. No. 4,327,078, which was referenced earlier, is illustrative of the different types of topical administrations which may be employed to administer a soluble elastin-based derivative. In each of the examples provided, the concentration of the elastin peptide fragment of the present invention would be preferably about 1.5% and the concentration of water would be increased to make up the difference.

It is preferable that the topical administration of the composition of the present invention occur repeatedly over a predetermined time period, preferably in the range of about one week to about one month. In the Sprague-Dawley rats used to generate FIG. 1, the rats were treated topically with a 1.3% concentration of the hydrophilic elastin peptide formulated by the method disclosed herein for a period of 30 days. Testing illustrated that the endogenous elastin (measured by microgram ($\mu$g) Elastin per milligram (mg) Skin Fat Free Dry weight) of each of the rats to which the administration was applied doubled over that of a control sample and to a sample which was treated with a 5% concentration of DHEA over a similar time period. Three animals each were used to generate the data for S CONTR, US CONT, and DHEA and eleven animals were used for HEP. Three skin samples from the treated areas of each animal were taken for study, and the three results from each animal were averaged. The mean of these results were: S CONTR (1.408); US CONTR (2.291); DHEA (1.753); HEP (3.175). The elastin content of the skin was determined by a precise assay for rat elastin developed by Sandberg, et al. ("Quantitation of Elastin in Tissues and Culture: problems related to the accurate measurement of small amounts of elastin with special emphasis on the rat" *Connective Tissue Research.* 25: 139–48, 1990) the assay portion of which is hereby incorporated herein by reference thereto. The data of FIG. 1 are significant at an alpha level less than 0.001 as determined by analysis of variance. This means there is less than one chance in a thousand that the findings occurred by chance.

This data further supports the use of the cosmetic or pharmaceutical preparation over an extended period preferably in the range of one week to one month, more preferably in the range of seven days to about fourteen days and most preferably about fourteen days of daily administration at about 1.5% concentration of elastin peptide or peptides having a molecular weight lower than about 10,000 Da, more preferably less than 1,000 Da and most preferably in the range of about 180 Da to about 600 Da.

Figure 2:
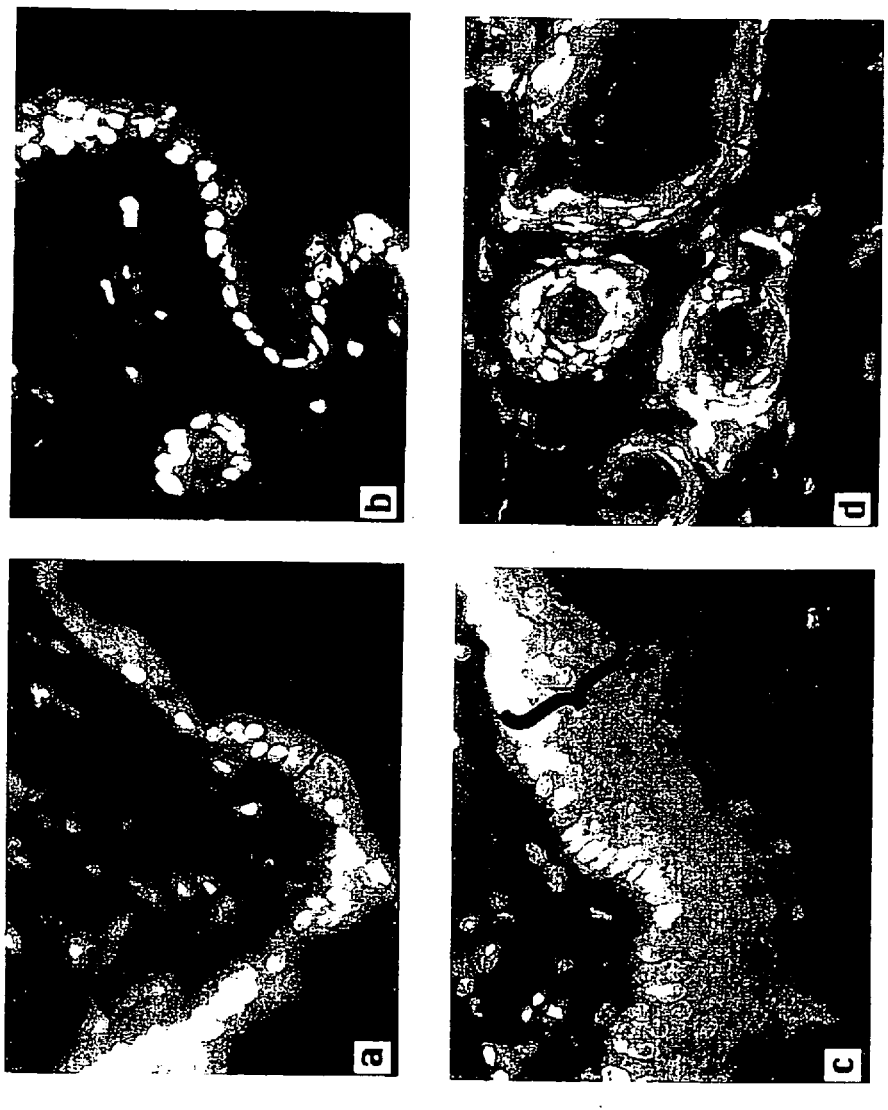
FIG. 2 is a micrograph illustrating the microvascular response of the skin tissue with the present invention.

FIG. 2 is a micrograph intended to illustrate the increased appearance, and thus beneficial cosmetic implications of the present invention. As can be seen from FIG. 2, skin treated with an elastin peptide fragment appears to be healthier than untreated skin. This is evidenced under a microscope by an increase in vascular response. In FIG. 2, fixed tissue sections of rat skin were labeled with flourescein conjugated antifibronectin antibodies. Panel a in FIG. 2 is a representative sample from the unshaven control tissue; panel b is a representative sample from the shaven control sample; and panel c is a representative sample of the tissue which received DHEA topical treatment. Finally, panel d received treatment with the present invention in a topical treatment in accordance with the samples discussed above with regard to FIG. 1. The dermal layer in the control panels (a and b) is relatively uniform and thin compared to the thickness of both panel c and panel d. For convenience, in each of panels a, b, c, and d, the dermal layer is bracketed. Surprisingly and illustrative of some of the benefits obtained utilizing the present invention, panel d illustrates an increased concentration of capillary venules in the subdermal region. The capillary venules are shown in this figure as brightly stained oval bodies that lie beneath the dermal layer. The increase in the concentration of endothelial cells in the subdermal region indicate an increase in capillary density and therefore illustrate the potential for the present invention to be used for the formation of blood vessels or capillary venules (neovascularization or angiogenesis).

It appears that the elastin peptide fragment of the present invention would preferably include sequences of Leucine-Glycine and/or Valine-Glycine-Valine-Hydroxyproline-Glycine, and/or Valine-Glycine-Valine-Proline-Glycine. It would also appear that sequences which contain Glycine and/or Proline are most preferred, and that a composition which includes either or both of these amino acids in a much larger concentration (relative to other amino acids present) are most preferred. While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. For example, the composition can be administered via many alternative drug delivery vehicles known in the art, and the composition may be used to treat tissue which is dependent upon elastin for its utility as opposed to its appearance and the elastin peptides can be derived from digestion of elastin synthesis of the amino acid sequence (either solid state or liquid), and from overexpression in a bacterial system. Accordingly, all such variances should be viewed as being within the scope of the present invention as set forth in the claims below.

The invention relates to the use in a cosmetic or dermatological composition for topical application intended to prevent or to treat the manifestations of cutaneous aging and/or the effects of UV irradiation on the skin, of 7α or 7β substituted compound of DHEA or PREG, reduced or not reduced in

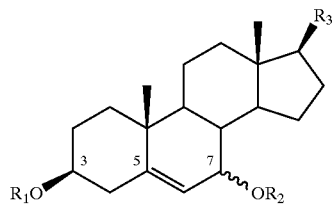

(I)

position 5, and therefore corresponding to the formula:
to the formula

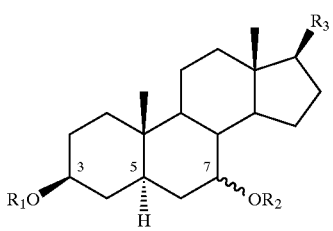

(II)

in which:

$R_1$ is chosen from among: a hydrogen atom, functional groups which are an ester of an organic acid with 1 to 24 carbon atoms, a sulphate ester or a phosphate ester, or a carbonaceous ether with 1 to 24 atoms of carbon that includes zero or several nitrogen atoms, carbohydrate ethers with 3 to 100 carbon atoms and their derivatives that contain or do not contain, one or several atoms of nitrogen.

$R_2$ is chosen from among: a hydrogen atom or a functional group that is an ester of a fatty acid with 1 to 24 carbon atoms.

$R_3$ is chosen from among: a hydrogen atom, an —OH group, groups of formula: —CO—$R_4$, —CHOH—$R_4$, =CH—$CH_3$, =COH—$CH_3$, —$CHR_4$—$CH_3$, =O, in which $R_4$ is a substituted or non-substituted alkyl group containing from 1 to 10 carbon atoms, preferably a methyl group.

Compounds which may be included in this invention are the 7α or 7β substituted derivatives of DHEA or PREG and more particularly 7Oα or 7β hydroxylated derivatives, reduced or not reduced in position 5.

One group of preferred compounds of the invention are the 7α-hydroxylated derivatives, that is to say those in which the oxygen in the 7 position is axial (7α) and the $R_2$ substituent is hydrogen.

Another group of preferred compounds of the invention are those where $R_1$ is hydrogen, notably 7α-hydroxy-DHEA and 7α-hydroxy-isoandrosterone where $R_3$ is a ketone (=O).

It should be noted that the derivatives of the invention in which $R_1$ is an organic acid have enhanced liposolubility which offers the advantage of improved retention of these compounds in the cells, notably at the membranes and consequently their activity and their effect on the cutaneous cells are prolonged. Among the derivatives, those in which $R_1$ is a palmitate, an oleate or a ferulate are preferred and notably 3β-palmitoyl-DHEA, 3β-pleyl-DHEA and 3β-feruloyl-DHEA.

The cosmetic and dermatological compositions of the invention can include one or several steroid derivatives as well as other compounds known for their cosmetic or dermatological property, such as hormones, and the additives or vehicles traditionally used in these fields.

For the use of a steroid derivative of the invention in a cosmetic composition intended to compensate for, treat and/or prevent the cutaneous effects of aging and/or the effects of UV irradiation on the skin, said derivative is administered at a dose of between 0.05 and 10 mg per application and per day and preferably between 0.05 and 5 mg per application and per day.

The restorative effect and the effect of preventing cutaneous aging in persons of a certain age as well as the protective effects in relation to UV is applicable to any treatment aimed at restoring cutaneous tone, firming up the skin and getting rid of wrinkles.

By their nature, the derivatives of the invention can be used in many different galenic forms for their percutaneous administration. One may mention forms that result from the addition to derivatives of the invention of compounds acceptable in cosmetics and which permit the production of creams, pastes, gels, lotions, "water-in-oil" and "oil-in-water" emulsions as well as forms composed of liposomes, simple or mixed micelles, or other penetration promoters such as lysophospholipids, cyclodextrins, polyethylene glycol, surface active agents, alcohols, fatty acids and vegetable oils. This list is not limitative and any other presentation known to man can be envisaged so long as it is adaptable to the steroidal derivatives of the invention which have the property of being, at the same time, hydrosoluble and liposoluble. Hence, cosmetic and dermatological compositions of the invention can be in the form of creams, lotions, gels and ointments or any other form generally used for topical applications. In addition, the present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. U.S. Pat. No. 4,327,078, incorporated herein as if set forth in its entirety, is illustrative of the different types of topical administrations which may be employed to administer the composition of the present invention. It is preferable that the topical administration of the composition of the present invention occur repeatedly over a predetermined time period, preferably in the range of about one week to about one month.

Other advantages and characteristics of the invention will become apparent on reading the examples which follow, given as non-limitative examples and showing the performance obtained by the derivatives of the invention as anti-apoptotic, anti-radical agents and promoters for the proliferation of human cutaneous cells.

EXAMPLE 1

7 hydroxy DHEA and 7 hydroxy isoandrosterone treated rat skin.

Upon histologic examination of hematoxylin and eosin (H&E) stained rat skin cross sections, a striking physical change was noted. The dermal layer of skin was thickened to nearly twice that of the untreated controls (both shaven and unshaven). This finding was consistent and most pronounced when the parent compound (DHEA) was used on young, healthy rats. However, it also occurred in replicate experiments when the derivatives were used. There was no change in the outer (keratin) layer nor increase of vascularity of the inner layer of the treated skin sections. The latter two findings support the toxicologic studies, done concomitantly, which found no significant toxicity when the compounds were used at 0.5% concentration in a suitable carrier applied twice daily (12 hour intervals) for 30 days. Further, the DHEA and derivatives induction of dermal thickening was completely reversible. A subset of experimental animals within each treatment group were left untreated for 30 days. Upon examination, treated skin sections were indistinguishable from the untreated.

EXAMPLE 2

DHEA 7 hydroxy DHEA and 7 hydroxy isoandro-sterone.

The ability of a compound to scavenge free radicals implicates it as an antioxidizing agent that could help to reduce the natural oxidizing effects of aging. In a first test of whether DHEA or it derivatives have the ability to capture free radicals, an in-vitro oxygen radical assay was devised, The assay was run in quadruplicate to perfect the concentrations of controls as well as test the diluents (phosphate buffered saline (PBS) and DMSO) in which the DHEA and its derivatives were dissolved. The positive controls used were homocysteine and ascorbic acid (Vitamin C). The results of replicate experiments revealed that PBS and DMSO did not affect the light emission from luminol (the chosen chemiluminescent indicator) when it reacted with the oxygen radical given off by hydrogen peroxide. However, when diluted luminol was pre-incubated with DHEA at 100 µg/ml, the light emission was reduced by 20%; 7 hydroxy isoandrosterone reduced the luminol reaction by 15%; the 7 hydroxy DHEA did not cause any reduction of luminol in the assay. These results indicate that both DHEA and 7 hydroxy isoandrosterone are free radical scavengers.

EXAMPLE 3

Chemical alterations in the skins of neonatal male Sprague-Dawley rats.

DHEA and the altered compounds of DHEA (the 7 hydroxy derivative and the 7 hydroxy-isoandrosterone) were found to have the ability to modify the elastin and collagen contents of neonatal rat skin when applied twice daily over a 30 day period at a concentration of 0.5% in a suitable carrier.

Collagen and elastin contents were measured on dry, defatted, hair-free skin samples. Collagen contents were assessed through hydroxyproline evaluations in hydrolyzed, 0.1N hot sodium hydroxide extracts. Elastin contents were measured by HPLC evaluation of the contents of thermolysin-produced peptides in digests of the hot sodium hydroxide residue. Controls were both shaven and unshaven, the shaven receiving only the carrier twice daily.

Using five animals per group, the results unequivocally showed that in the treated groups, collagen is increased by 24% for the 7 hydroxy and the 7 hydroxy-isoandrosterone whereas DHEA itself induced a decrease of 16%. Elastin contents were increased by all the compounds (28% for DHEA, 30% for the 7 hydroxy and the 7 hydroxy-isoandrosterone). In these studies statistical analysis of variance was significant at an alpha level of 0.01. Similar to the histologic observations, these chemistries are reversible. Collagen and elastin contents returned to near normal levels after cessation of treatment for 30 days.

EXAMPLE 4

Effects of 3β,7α-dihydroxy-5-androstene-17-one (7α-hydroxy-DHEA) and of 3β,7α-dihydroxy-5α-androstane-17-one (7α-hydroxy-ISOA) on the cellular apoptosis induced by glucocorticoids.

The thymus of a mouse C57BL/6 age four weeks was removed. Culture of the thymocytes was carried out for 6 hours in a RPMI 1640 medium and in the presence or in the absence of the steroid tested. The apoptosis (fragmentation of the DNA) was measured by flow cytometry after marking with propidium iodide. The apoptotic phenomenon was controlled by electrophoresis of the DNA developed by ethidium bromide according to the traditional technique (observation of ladders of 200 pairs of bases). The results reported in Table A below were obtained:

TABLE A

| Steroids in the medium (in 10 ml of ethanol) | Apoptotic cells (%) |
| --- | --- |
| Ethanol alone | 41.5 |
| Dexamethasone $10^{-6}$ M | 72.7 |
| Dexamethasone $10^{-6}$ M + DHEA $10^{-6}$ M | 39.0 |
| Dexamethasone $10^{-6}$ M + 7α hydroxy-DHEA $10^{-6}$ M | 58.8 |
| Dexamethasone $10^{-6}$ M + 7α-hydroxy-ISOA $10^{-6}$ M | 72.0 |
| Dexamethasone $10^{-5}$ M | 73.5 |
| Dexamethasone $10^{-5}$ M + DHEA $10^{-5}$ M | 51.4 |
| Dexamethasone $10^{-5}$ M + 7α-hydroxy-DHEA $10^{-5}$ M | 48.6 |
| Dexamethasone $10^{-5}$ M + 7α-hydroxy-ISOA $10^{-5}$ M | 46.3 |

It appears from these tests that the 7α-hydroxysteroids tested have an anti-apoptotic effect that opposes that of dexamethasone on the T cells of mice. Their effect at $10^{-5}$ M is greater than that of their steroid precursor (DHEA or dehydro-epiandrosterone or 3β-hydroxy-5-androstene-17-one).

EXAMPLE 5

Effects of 3β,7α-dihydroxy-5-androstene-17-one (7α-hydroxy-DHEA) on the viability of human keratinocytes in culture.

Human keratinocytes were obtained from surgical items and were cultivated in a monolayer until preconfluence. The 7α-hydroxy-DHEA was administered to these cultures at various concentrations in ethanolic solution (10%), each concentration being tested eight times. Controls were carried out with ethanol alone (10%). After twenty-four hours, the viability of the keratinocytes was measured by testing with MTT (3-(4,5-dimethylthiazol-2-yl)-2,5 diphenyl tetrazolium bromide) where the mitochondrial dehydrogenase succinate converts the MTT into blue crystals of formazan soluble in DMSO (Mosmann, *J. Immunol. Methods* 65: 55–63, 1983). The results of the tests on the viability of the keratinocytes are reported in Table B below. The cellular viability is calculated according to the formula:

$$\% \text{ viability} = DO_{540} \text{ product} \times 100 / DO_{540} \text{ control.}$$

Any value greater than 100 indicates a product that encourages cellular viability.

TABLE B

| Steroids in the medium (in 10% ethanol) | Viability of the keratinocytes (%) |
| --- | --- |
| 10% ethanol alone (control) | 100 |
| 7α-hydroxy-DHEA $10^{-4}$ M | 124 ± 10 |
| 7α-hydroxy-DHEA $5 \cdot 10^{-5}$ M | 111 ± 7 |
| 7α-hydroxy-DHEA $10^{-5}$ M | 119 ± 7 |
| 7α-hydroxy-DHEA $5 \cdot 10^{-6}$ M | 147 ± 9 |
| 7α-hydroxy-DHEA $10^{-6}$ M | 154 ± 6 |
| 7α-hydroxy-DHEA $5 \cdot 10^{-7}$ M | 139 ± 3 |
| 7α-hydroxy-DHEA $10^{-7}$ M | 147 ± 5 |
| 7α-hydroxy-DHEA $10^{-8}$ M | 127 ± 3 |

These results show that 7α-hydroxy-DHEA significantly increases the viability of human keratinocytes at concentrations between $10^{-4}$ M and $10^{-8}$ M, the maximum (viability increases of between 54% and 39%) being obtained between 5. $10^{-6}$ M and $10^{-7}$ M. Furthermore, no cytotoxicity was observed. Other comparative tests have demonstrated that the precursor DHEA had no effect (100±5).

EXAMPLE 6

Effects of 3β,7α-dihydroxy-5-androstene-17-one (7α-hydroxy-DHEA) on the proliferation of human fibroblasts in culture.

The cultures of human fibroblasts (32 year old woman) were seeded on twenty-four site plates at the rate of 50,000 cells per site in a standard culture medium (DMEM, gentamycine, amphotericine B, penicillin, L-glutamine, 10% SVF). The tests were carried out on four series of three sites. After twenty-four hours, the fibroblasts adhered to the support and three series were treated with 7α-hydroxy-DHEA at concentrations of $10^{-6}$ M, 6. $10^{-6}$ M and $10^{-7}$ M. The fourth series only contained the vector (ethanol). The media were renewed daily, and at ninety-six hours (seventy-two hours of test contact with the 7α-hydroxy-DHEA), the fibroblasts were counted on a Malassez cell in the presence of blue trypan.

The results of the effects on the proliferation of fibroblasts are reported in Table C below.

TABLE C

| Steroids in the medium | Number of Fibroblasts | Increase in the viability (%) |
|---|---|---|
| Control | 190,667 ± 6,766 | / |
| 7α-hydroxy-DHEA $10^{-7}$ M | 230,667 ± 8,511 | +21 |
| 7α-hydroxy-DHEA $10^{-6}$ M | 268,000 ± 27,154 | +41 |
| 7α-hydroxy-DHEA 5 · $10^{-6}$ M | 258,667 ± 3,351 | +36 |

These results demonstrate that, under the experimental conditions, the treatment of fibroblasts by 7α-hydroxy-DHEA at $10^{-7}$ M, $10^{-6}$ M and 5. $10^{-6}$ M increases the cellular proliferation by respectively 21%, 41% and 36% with respect to the untreated control fibroblasts.

EXAMPLE 7

The anti-radical effects of 3β,7α-dihydroxy-5-androstene-17-one (7α-hydroxy-DHEA) on a suspension of human keratinocytes.

Keratinocytes from a healthy donor (25 year old woman) were cultivated to the subconfluent stage in a specific medium (KGM) for the proliferation of keratinocytes. The suspensions obtained were split up, in triplicate, into four series, of which three were irradiated for thirty minutes with a lamp omitting UVA so as to speed up the production of free radicals. Among the three irradiated series, one contained Vitamins C and E (0.7%) and was used as a protection reference, one contained 7α-hydroxy-DHEA at $10^{-6}$ M and the last served as a control. Table D below reports on the measurement of the anti-radical effects.

The free radicals produced generate lipoid peroxides which are measured by chemiluminescence (Belghmi et al. *J Biolum. Chemilum.* 2: 113–119, 1982). The effectiveness of the 7α-hydroxy-DHEA was calculated on the basis of non-irradiated controls and the protection reference.

TABLE D

| Keratinocytes | Chemiluminescence | Effectiveness |
|---|---|---|
| Non irradiated controls | 2,529 ± 153 | / |
| Irradiated controls | 427,750 ± 137,322 | / |

TABLE D-continued

| Keratinocytes | Chemiluminescence | Effectiveness |
|---|---|---|
| Irradiated + 0.7% Vit. C + E | 2,970 ± 288 | 100% |
| Irradiated + 7α-hydroxy-DHEA $10^{-6}$ M | 44,164 ± 13,303 | 90% |

Under the conditions of this study, in vitro anti-radical effectiveness of 7α-hydroxy-DHEA at $10^{-6}$ M is 90%. 7α-hydroxy-DHEA can be considered as a good anti-radical product.

While the foregoing has been set forth in considerable detail, the embodiments, procedures, formulations and compositions are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

As used herein, the term "subject" or "patient" means any mammal, including humans, in which elastin is utilized for proper tissue function. The methods herein for use contemplate prophylactic use as well as curative use in therapy of an existing condition.

As used herein, the term "about" means plus or minus 10% of the numerical value of the number with which it is being used. Therefore, about 50% means in the range of 45%–55%. As used herein, the term "Dalton" (or "Da") refers to the unit of mass which is equivalent to the mass of a hydrogen atom ($1.66 \times 10^{-24}$ gram). Generally speaking, the term "tissue" refers to any aggregation of similarly specialized cell which are united in the performance of a particular function. Unless otherwise indicated, the term "skin" means that outer integument or covering of the body, consisting of the dermis and the epidermis and resting upon subcutaneous tissue.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with a composition, can include, but is not limited to, providing a composition into or onto the target tissue; providing a composition systemically to a patient by, e.g., intravenous injection whereby the therapeutic reaches the target tissue; providing a composition in the form of the encoding sequence thereof to the target tissue (e.g., by so-called gene-therapy techniques) whereby the elastin peptide fragment is expressed within the target tissue.

Details on techniques for formulation and administration of pharmaceuticals may be found in the latest edition of *Remington's Pharmaceutical Sciences* (Mack Publishing Co, Easton Pa.). Although local topical delivery is desirable, there are other means of delivery, for example: oral, parenteral, aerosol, intramuscular, subcutaneous, transcutaneous, intamedullary, intrathecal, intraventricular, intravenous, intraperitoneal, or intranasal administration.

As used herein, the term "therapeutic" means an agent utilized to treat, combat, ameliorate, prevent or improve an unwanted condition or disease of a patient. The condition being treated in the present invention is deficient elastin in tissue, that is, a need in the tissue for more elastin. As it applies to skin, it is measured by turgor, tone, appearance, degree of wrinkles, and youthfulness.

Finally, the term "cosmetic," as used herein, refers to a beautifying substance or preparation which preserves, restores, bestows, simulates, or enhances the appearance of bodily beauty, specifically as it relates to the appearance of tissue or skin.

Incorporated by reference as if set forth in their entirety are International Publication Nos. WO 96/35428 and WO 94/08588.

What is claimed is:

1. A therapeutic composition comprised of a compound corresponding to the formula:

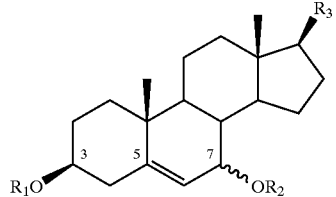
(I)

or the formula

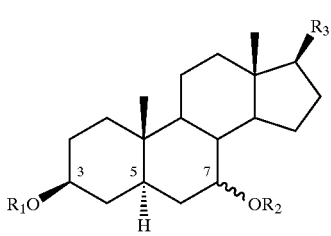
(II)

in which
- R1 is selected from the group consisting of: a hydrogen atom, functional groups which are an ester of an organic acid with 1 to 24 carbon atoms, a sulphate ester, a phosphate ester, a carbonaceous ether with 1 to 24 atoms of carbon that includes or does not include nitrogen atoms, carbohydrate ethers with 3 to 100 carbon atoms;
- R2 is selected from the group consisting of: a hydrogen atom or a functional group that is an ester of a fatty acid with 1 to 24 carbon atoms;
- R3 is selected from the group consisting of: a hydrogen atom, an —OH group, groups of formula: —CO—R4, —CHOH—R4, =CH—CH3, =COH—CH3, —CHR4—CH3, =O, in which R4 is a substituted or non-substituted alkyl group containing from 1 to 10 carbon atoms;
- an elastin peptide fragment selected from the group consisting of SEQ ID NO:17 (Valine-Valine-Proline-Glutamine), SEQ ID NO:18 (Valine-Alanine-Alanine-Arginine-Proline-Glycine), SEQ ID NO:19 (Leucine-Glycine-Alanine-Glycine-Glycine-Alanine-Glycine), and SEQ ID NO: 23 (Valine-Glycine-Valine-Hydroxyproline-Glycine); and
- a carrier.

2. The composition of claim 1, wherein said elastin peptide fragment is at a therapeutically effective concentration.

3. The composition of claim 2, wherein said therapeutically effective concentration is a range of about 0.0002% to about 90% by weight.

4. The composition of claim 3, wherein said therapeutically effective concentration is in the range of about 0.5% to about 10% by weight.

5. The composition of claim 1, wherein said composition is a cosmetic preparation.

6. The composition of claim 5, wherein said cosmetic preparation is selected from the group consisting of an emulsion, lotion, spray, aerosol, powder, ointment, cream and foam.

7. The composition of claim 1, wherein said composition further comprises a delivery system selected from the group consisting of a topical delivery system, a subcutaneous delivery system, a transcutaneous delivery, an oral delivery system, a nasal delivery system, an aerosol delivery system, and a patch delivery system.

8. The composition of claim 1 further comprising a second elastin peptide fragment selected from the group consisting of SEQ ID NO:1 (Alanine-Valine-Glycine), SEQ ID NO:2 (Valine-Glycine-Alanine-Glycine), SEQ ID NO:3 (Isoleucine-Glycine-Glycine), SEQ ID NO:4 (Leucine-Glycine), SEQ ID NO:5 (Isoleucine-Glycine-Alanine-Glycine), SEQ ID) NO:6 (Leucine-Glycine-Glycine), SEQ ID NO:7 (Valine-Alanine-Proline-Glycine), SEQ ID NO:8 (Leucine-Glycine-Proline-Glycine), SEQ ID NO:9 (Leucine-Glycine-Alanine-Glycine), SEQ ID NO:10 (Valine-Glycine-Proline-Glycine), SEQ ID NO:11 (Phenylalanine-Glycine-Proline-Glycine) SEQ ID NO:12 (Valine-Glycine-Proline-Glutamine), SEQ ID NO:13, (Leucine-Glycine-Alanine), SEQ ID NO:14 (Valine-Glycine-Proline-Alanine), SEQ ID NO:15 (Valine-Valine-Proline-Glycine), SEQ ID NO:16, (Alanine-Valine-Proline-Glycine), SEQ ID NO:17 (Valine-Valine-Proline-Glutamine), SEQ ID NO:18 (Valine-Alanine-Alanine-Arginine-Proline-Glycine), SEQ ID NO:19 (Leucine-Glycine-Alanine-Glycine-Glycine-Alanine-Glycine), SEQ ID NO:20 (Alanine-Isoleucine-Proline-Glycine), SEQ ID NO:21 (Leucine-Glycine-Proline-Glycine-Glycine), SEQ ID NO:22 (Alanine-Alanine-Alanine-Glutamine-Alanine), SEQ ID NO: 23 (Valine-Glycine-Valine-Hydroxyproline-Glycine), SEQ ID NO:24 (Valine-Tyrosine-Proline-Glycine-Glycine), SEQ ID NO:25 (Isoleucine-Glycine-Glycine-Valine-Glycine-Glycine), SEQ ID NO:26 (Valine-Alanine-Proline-Glycine-Valine-Glycine), SEQ ID NO:27 (Leucine-Glycine-Valine-Glycine-Glycine), SEQ ID NO:28 (Valine-Leucine-Proline-Glycine), SEQ ID NO:29 (Phenylalanine-Arginine-Alanine-Alanine-Alanine), SEQ ID NO:30 (Valine-Glycine-Glycine-Valine-Proline-Glycine), SEQ ID NO:31 (Phenylalanine-Glycine-Proline-Glycine-Glycine), SEQ ID NO:32 (Valine-Glycine-Valine-Proline-Glycine), SEQ ID NO:33 (Valine-Leucine-Proline-Glycine-Alanine-Glycine), SEQ ID NO:34 (Valine-Glycine-Leucine-Hydroxyproline-Glycine), SEQ ID NO:35 (Leucine-Glycine-Valine-Glycine-Alanine), SEQ ID NO:36 (Alanine-Phenylalanine-Proline-Glycine), SEQ ID NO:37 (Alanine-Phenylalanine-Proline-Glycine-Alanine), SEQ ID NO:38 (Valine-Glycine-Isoleucine-Proline-Alanine), SEQ ID NO:39 (Valine-Glycine-Glycine-Isoleucine-Proline-Threonine), SEQ ID NO:40 (Valine-Glycine-Valine-Glycine-Valine-Proline-Glycine), and SEQ ID NO:41 (Leucine-Glycine-Proline-Glycine-Valine-Glycine), wherein said second elastin peptide fragment is different from said elastin peptide fragment.

9. The composition of claim 8, wherein said elastin peptide fragment and said second elastin peptide fragment are of a therapeutically effective range of about 0.0002% to 90% by weight.

10. The composition of claim 8, wherein said composition is a cosmetic preparation.

11. The composition of claim 10, wherein said cosmetic preparation is selected from the group consisting of an emulsion, lotion, spray, aerosol, powder, ointment, cream and foam.

* * * * *

UNITED STATES PATENT AND TRADEMARK OFFICE
CERTIFICATE OF CORRECTION

PATENT NO. : 6,777,389 B1
DATED : August 17, 2004
INVENTOR(S) : Mitts et al.

Page 1 of 1

It is certified that error appears in the above-identified patent and that said Letters Patent is hereby corrected as shown below:

Column 13,
Line 43, change "70α" to -- 7α --.

Signed and Sealed this

Fifth Day of April, 2005

JON W. DUDAS
*Director of the United States Patent and Trademark Office*